Oct. 24, 1939.
E. L. RUSSELL
STRAWBERRY
Filed June 23, 1938
Plant Pat. 345
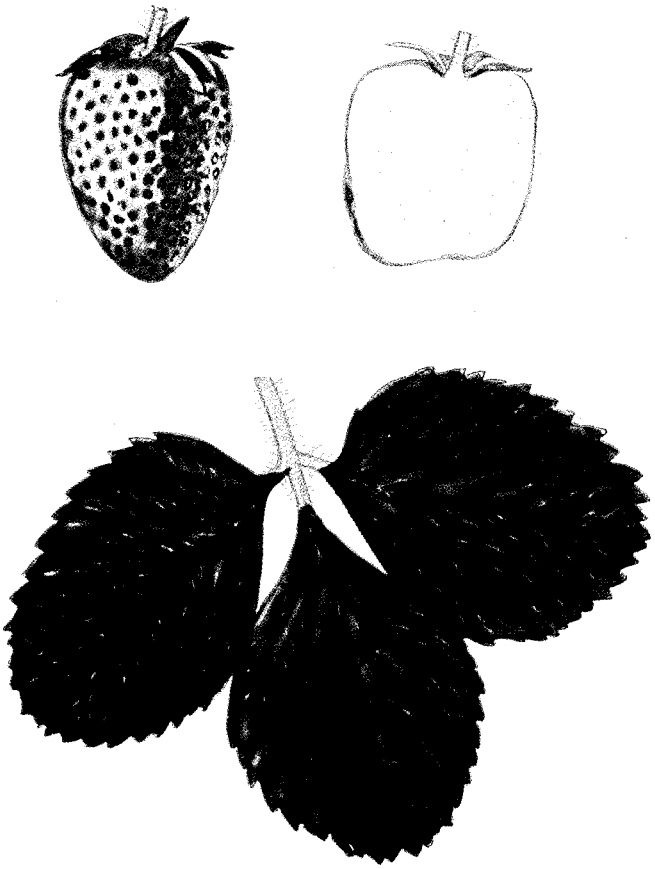
INVENTOR
E. L. Russell
BY L. F. Randolph
ATTORNEY Patented Oct. 24, 1939

Plant Pat. 345

UNITED STATES PATENT OFFICE

345

STRAWBERRY

Evan L. Russell, Jonesville, Va.

Application June 23, 1938, Serial No. 215,451

1 Claim. (Cl. 47—62)

My present invention consists in the production of a new and desirable variety of commercial strawberries, and has for its object the provision of a variety of strawberry plant suitable for commercial use, the plants being of extreme hardiness, deep-rooted and thereby standing dry weather, the roots reaching to an unusual depth into the soil; that is extremely prolific in production of runners and seedlings; and a plant producing fruit that is unusually large and rich red colored, and of superior texture and flavor.

The strawberry plant is a chance seedling that was discovered by me in 1933, a single plant growing on my farm in an uncultivated plot near where "Premier" strawberry plants had been growing and is therefore, undoubtedly a variation of that variety of berry. Illustrated in the accompanying drawing is shown in detail a leaf, a typical berry of conical shape, and a halved berry of wedge-shape, disclosing the texture and coloring of a ripe berry.

As hereinbefore stated the parent plant of my new variety of strawberry was discovered by me on my farm, known as "Ridgeway Farm", Jonesville, Lee County, Virginia, during the year 1933. I set the parent plant out in a segregated location and carefully preserved it from mixture with other plants and, since March, 1938, I have been selling propagations of runner plants to others, particularly in my immediate neighborhood.

As the single plant was near a plot on which I had previously been raising "Premier" strawberries I am convinced that my discovered variety is a seedling of said variety, but differs therefrom in that the foliage is of a rich dark green color; it produces three or four times as many runner plants, and the fruit is much larger and of better quality than Premier berries, and noticeably sweeter and more fragrant. My discovery of plant differs from "Premier" plants because it ripens later than the "Premier", and is in fact a mid-season variety. It also differs from "Premier" by being free from leaf spot.

The following is a detailed description of the principal features and characteristics of my new variety of strawberry.

*Plant.*—Of medium to large size, the stems upstanding and vigorous in growth. The plants have large crowns and long heavy and vigorous roots that extend to a great depth into the soil and for that reason the plants resist drought thereby assuring an unusually heavy crop of berries.

*Leaves.*—Large and a rich dark green in color, the edges of the leaves remote from the stem being substantially circular in contour and tapering from said circular portions on one or both sides to the branch stem, being distinguished from the usual pointed leaf of the "Premier" variety of plants. The upper faces of the leaves have fine light yellow colored hairs scattered over their surfaces, and the stems are stocky and also provided with hairs that appear on the branch leaf stems, as well as the main stem. The rounded edges of the leaves are irregularly serrated or notched, the notches varying in number from twenty to twenty-five on each leaf. The leaf veins are well marked, are of a darker shade of green, more nearly black, than the parenchyma, and are delicately outlined on the leaves.

*Runners.*—A distinguishing characteristic is the prolific production of runners, being larger in number and longer, and producing more runner plants than most other varieties.

*Calyx.*—Usually consists of a single row or layer of sepals.

*Flowers.*—Are "perfect", that is both staminate and pistillate and are late blooming. The stems are sturdy and upstanding so that the fruit is raised to an unusual height above the surface of the ground so as to be kept free from the soil and sand.

*Fruit.*—While the plant is late blooming the fruit ripens in midseason, the harvest of berries extending over a long period. The berries are extremely large of either a long conical shape or of wedge-shape as shown in the drawing. The berries are bright golden red in color and the meat of the berry near its outer surface is of a lighter shade of red having streaks of a still lighter hue extending from the outer surface inwardly towards the center, the center shading to a pinkish red. The berry stems like the leaf stem are covered thinly with light green colored hairs. Furthermore the fruit stems are of medium height and stocky, and they branch out in different directions so that the fruit on the stems appear as though sown broadcast through the plants and not in clusters or bunches as in other varieties. The plant has a long bearing season, the fruit holding its size throughout the season. The flesh of the berry is firm and meaty thus providing superior shipping qualities, as I have shipped the berries by motor truck for more than 300 miles and they arrived at their destination in perfect condition and brought top prices on the market. The berries are deliciously flavored, being very sweet, somewhat acid, but not objectionably so, as distinguished from the acid to sour flavor of the Premier fruit and have somewhat of the flavor of wild strawberries. In actual test of yield of my variety with other well-known varieties the results have shown that my variety produces from 100 per cent to more than 400 per cent more fruit than said other varieties.

Among the important, distinguishing features of my new variety of strawberry plant and fruit are the following:

1. The plants are very large and prolific, having large crowns, a deep heavy root system capable of producing a large crop of fine berries and resisting drought.

2. The leaves are more circular than the other varieties, and are rich dark green in color.

3. The berries are very large and firmly meated, being either long, conical, or wedge-shaped, the flesh being red adjacent to the outer surface of the berry shading to a pink, the red portions being streaked lighter colored and extending from the outer surface towards the middle of the berry. The stems are also hairy like the leaf stems.

4. The plants flower later than "Premier" and begin to ripen later as a mid-season variety and continue to produce for a long period.

5. The flowers are "perfect" and their stems exceedingly sturdy and upstanding to support the fruit from contact with the surface of the plant bed.

6. The plants are free from diseases including yellow leaf and leaf spot.

7. The fruit stems are sturdy and upright, sending out smaller branches from the top of the main stem for each individual berry, said branches extending outwardly in all directions and holding the young berries very erect, giving a matted row of plants the appearance of an even distribution of the berries over the row. This distinguishes my variety from Premier, Dorsett, Fairfax, Redheart, Missionary, and many other varieties of which I have had knowledge by growing the plants on my farm, that have the berries in large clusters or bunches.

Having thus described my invention and illustrated it in the drawing filed herewith, I claim:

The variety of strawberry plant, characterized by its large crown, its long, heavy and vigorous root system, the leaves being large and supported on sturdy stems, the coloring of the leaves being a dark rich green provided with delicate veins of a darker hue, the leaves having their free edges circular in contour and irregularly serrated or notched, the plants being free from leaf spot, the flowers being "perfect" with sturdy upstanding stems that distribute the berries evenly over a row of plants, the fruit of unusual size, of bright golden red color, the flesh of the berries being red near the outer surface of the berry, shot through with light colored radial streaks, and shaded towards the center to a light pink, the berries also being of distinctly delicious, somewhat wild, flavor, and possessing superior shipping qualities.

EVAN L. RUSSELL.